US009561684B2

(12) United States Patent
Rivera, III (10) Patent No.: US 9,561,684 B2
(45) Date of Patent: Feb. 7, 2017

(54) SYSTEM AND METHOD FOR VARYING HOLOGRAM VISIBILITY

(71) Applicant: Seferino Rivera, III, Sugar Land, TX (US)

(72) Inventor: Seferino Rivera, III, Sugar Land, TX (US)

( * ) Notice: Subject to any disclaimer, the term of this patent is extended or adjusted under 35 U.S.C. 154(b) by 7 days.

(21) Appl. No.: 13/924,525

(22) Filed: Jun. 21, 2013

(65) Prior Publication Data

US 2013/0280446 A1      Oct. 24, 2013

Related U.S. Application Data

(63) Continuation-in-part of application No. 13/454,030, filed on Apr. 23, 2012, now abandoned.

(60) Provisional application No. 61/517,589, filed on Apr. 22, 2011.

(51) Int. Cl.
| | | |
|---|---|---|
| *B44F 1/10* | (2006.01) |
| *B62J 17/04* | (2006.01) |
| *A42B 3/22* | (2006.01) |
| *A61F 9/02* | (2006.01) |
| *B62J 99/00* | (2009.01) |

(52) U.S. Cl.
CPC . *B44F 1/10* (2013.01); *A42B 3/22* (2013.01); *A42B 3/226* (2013.01); *A61F 9/023* (2013.01); *B62J 17/04* (2013.01); *B62J 2099/0086* (2013.01); *Y10T 156/10* (2015.01)

(58) Field of Classification Search
CPC ..................................... A42B 3/22; B44F 7/00
See application file for complete search history.

(56) References Cited

U.S. PATENT DOCUMENTS

| | | | | |
|---|---|---|---|---|
| 4,802,755 A | * | 2/1989 | Hensler | G02C 7/102 |
| | | | | 351/159.61 |
| 5,024,895 A | * | 6/1991 | Kavanagh et al. | 428/437 |
| 5,035,474 A | | 7/1991 | Moss | |
| 5,269,858 A | | 12/1993 | Silverman | |
| 5,432,623 A | * | 7/1995 | Egan | G02C 7/00 |
| | | | | 351/41 |
| 5,731,060 A | | 3/1998 | Hirukawa | |
| 5,896,587 A | | 4/1999 | Gentry | |

(Continued)

FOREIGN PATENT DOCUMENTS

| | | |
|---|---|---|
| WO | WO 9626462 A1 | 8/1996 |
| WO | WO 0218986 A2 | 3/2002 |

OTHER PUBLICATIONS http://web.archive.org/web/20020827054351/http://www.tricktape.com/product.asp?0=234&1=386&3=996.*

*Primary Examiner* — Ian Rummel
(74) *Attorney, Agent, or Firm* — Spradley PLLC; Michael Spradley (57) ABSTRACT

A system and method for varying hologram visibility is disclosed herein. Specifically the system can comprise a shield. The shield can comprise a first layer and a second layer. The first layer can comprise a photochromic material having a dark state and a light state. The second layer can comprise a hologram that is less visible the first layer is in the light state. The method can comprise attaching a second layer to a first layer. The first layer can comprise a photochromic material having a dark state and a light state. The second layer can comprise a hologram. The hologram can be less visible when the first layer is in the light state than when the first layer is in the dark state.

13 Claims, 11 Drawing Sheets

(56) References Cited

U.S. PATENT DOCUMENTS

2004/0240067 A1* 12/2004 Marusi et al. ............... 359/588
2005/0009964 A1    1/2005 Sugimura

* cited by examiner

Fig. 9B

SYSTEM AND METHOD FOR VARYING HOLOGRAM VISIBILITY

PRIORITY

This patent application claims priority under 35 USC 119 from U.S. Utility application Ser. No. 13/454,030, which claims priority from U.S. Provisional Patent Application Ser. No. 61/517,589 filed Apr. 22, 2011, of common inventorship herewith entitled, "Sefe Visor."

FIELD OF THE DISCLOSURE

The present invention pertains to the field of polyester film products containing images, and more specifically to the field of moving three dimensional holographic images in a clear or tinted, polarizing polymeric thin film applied to cycling helmets, visors, ski goggles, windshields, etc. the helmet, visor, ski goggles, etc can be made of a photochromic material.

BACKGROUND OF THE INVENTION

The sky is the limit for today's sport enthusiasts and athletes, and the more extreme the activity, the better. Not only do these sport enthusiasts and athletes enjoy pushing the envelope on the risks they take, but they insist on blazing a trail with a premium of individual style. Skiers and snowboarders may be bundled from head to toe, but still can be distinguished by their gear and by the graphics on their skis and snowboards. Long before the days of chopper builders on reality TV, motorcyclists always have taken pride in individually customizing their bikes, watercraft or other equipment as a personal statement. One thing that skiers, snowboarders, boaters, jet skiers and motorcyclists share is the need for clear vision and vision protection. For skiers and snowboarders the protection takes the form of goggles. For motorcyclists and boaters the protection takes the form of helmet visors and windscreens.

The prior art has put forth several designs for cyclist helmets, and tint and image applications. Among these are:

U.S. Pat. No. 5,269,858 to Gary S. Silverman describes a method of simulating stained glass art by applying liquid paints to the object which may be a glass window or sheet. The leading paint dries in approximately two to three hours and then colored paints are applied as a covering over the areas which are peripherally defined by the leading paint.

U.S. Pat. No. 5,896,587 to Debra Gentry describes a bicycle helmet having a transparent eye shade and various interchangeable sun shield portions, along with affixed and built in sun shield portions. Stickers of various styles can be adhered to all eye shade portions.

U.S. Pat. No. 5,035,474 to Gaylord E. Moss, Brian D. Cohn, Mao-Jin J. Chern, Lacy G. Cook, and John J. Ferrer describes a binocular holographic helmet mounted display used by pilots while flying in low light level environments. This mounted display also combines infrared or other image detection and instrumentation symbology which enhance a pilot's flight vision.

None of these prior art references describe the present invention.

SUMMARY

A system and method for varying hologram visibility is disclosed herein. Specifically the system can comprise a shield. The shield can comprise a first layer and a second layer. The first layer can comprise a photochromic material having a dark state and a light state. The second layer can comprise a hologram that is less visible the first layer is in the light state.

The method can comprise attaching a second layer to a first layer. The first layer can comprise a photochromic material having a dark state and a light state. The second layer can comprise a hologram. The hologram can be less visible when the first layer is in the light state than when the first layer is in the dark state.

DETAILED DESCRIPTION

Described herein is a system and method for fading and strengthening a hologram. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
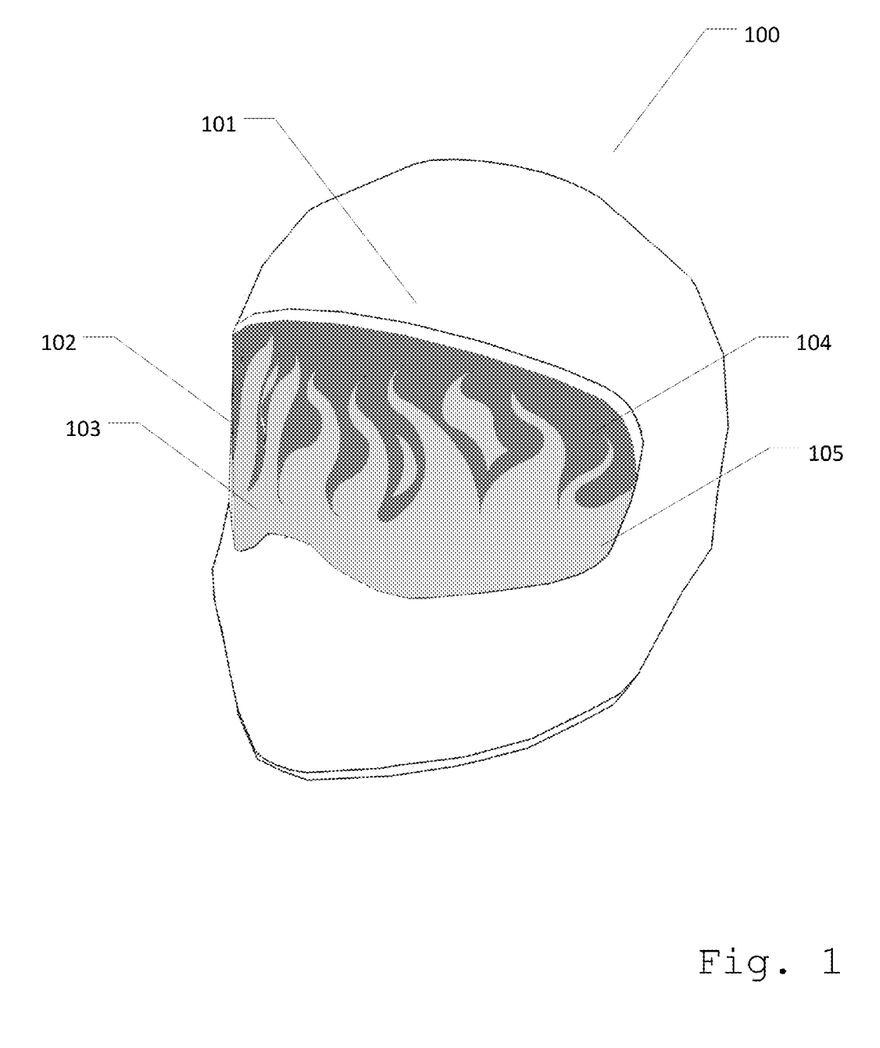
FIG. 1 illustrates a motorcycle helmet.

FIG. 1 illustrates a motorcycle helmet 100. For purpose of this disclosure, motorcycle helmet 100 can be a protective headgear used by motorcycle riders. Motorcycle helmet 100 can be any type of headgear that can be used by motorcycle riders. Various type of headgear includes but is not limited to full-face helmet, off-road or motocross helmet, modular helmet, or open-face helmet. Motorcycle helmet 100 can comprise a body 101 and a shield 102. Body 101 can be the base portion of motorcycle helmet 100 that covers the skull or head area of the user. Shield 102 can be attached at the front portion of body 101. As such, shield 102 can be made of transparent material such as glass, polycarbonate, or plastics. Shield 102 can either cover the whole face or can only cover the eye area of the user. Shield 102 can be used to protect the rider from wind or small particles such as dusts, insects, or rocks, when driving or while doing any activities. Moreover, shield 102 can be used to screen out ultraviolet radiations (UV). In one embodiment, shield 102 can be removable from body 101. In such embodiment, shield 102 can be removed and can be replaced with another shield. In another embodiment, shield 102 can be permanently attached to body 101. Shield 102 can comprise a hologram 103, which can enhance or personalize the look of motorcycle helmet 100. Hologram 103 can be a three dimensional (3D) graphical image projected on shield 102.

Further, shield 102 can comprise a first layer 104 and a second layer 105. First layer 104 can be the innermost layer of shield 102. First layer 104 can comprise a photochromic material that allows shield 102 to change color upon and depending on the exposure of light. Second layer 105 can be the outermost layer of shield 102 covering first layer 104. Second layer 105 can comprise a holographic material that enables any graphical images to be seen in three dimensional (or 3D) forms. In one embodiment, hologram can be substantially transparent. As seen in FIG. 1, hologram 103 can be placed on second layer 105 of shield 102. The layer structure described herein can aid in strengthening the image of any holographic images when shield 102 is exposed to light by causing reflection. Inversely, when shield 102 is hidden from light the holographic image on second layer 105 can fade. In one embodiment, hologram 103 can be etched into photochromic material. As such, first layer 104 and second layer 105 are combined into one continuous object. In another embodiment, hologram 103 can be a combination of photochromic and non-photochromic material to cause reflection in a darkened state and non-reflection in a lightened state as discussed below.

Further, for purposes of this disclosure, the light mentioned herein can be light comprising ultraviolet (UV) radiations such as sunlight. Since photochromic material reacts with ultraviolet (UV) radiations, shield 102 and hologram 103 can react differently or may not have any reactive response when exposed to room lights that does not contain ultraviolet (UV) rays. Moreover, hologram 103 and any holographic image placed on second layer 105 do not affect the vision of the user.

Figure 2:
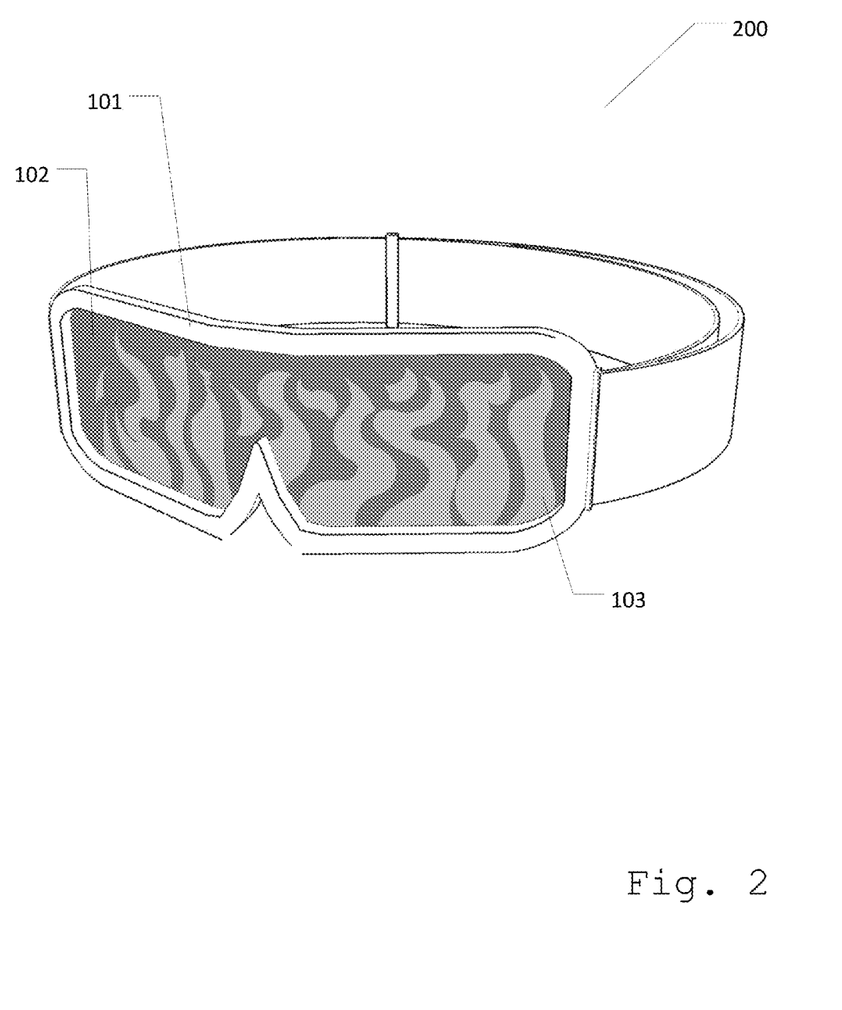
FIG. 2 illustrates a pair of goggles with a hologram.

FIG. 2 illustrates a pair of goggles 200 with hologram 103. For purpose of this disclosure, goggles 200 can be a type of eyewear that can either be used to protect the eye, or to enhance vision. Moreover, goggles 200 can also comprise body 101 and shield 102. In this embodiment, body 101 can be the frame that encloses or surrounds shield 102. Goggles 200 can be worn around the head and fit snuggly in the eye area. Further, shield 102 of goggles 200 can comprise hologram 103.

Figure 3:
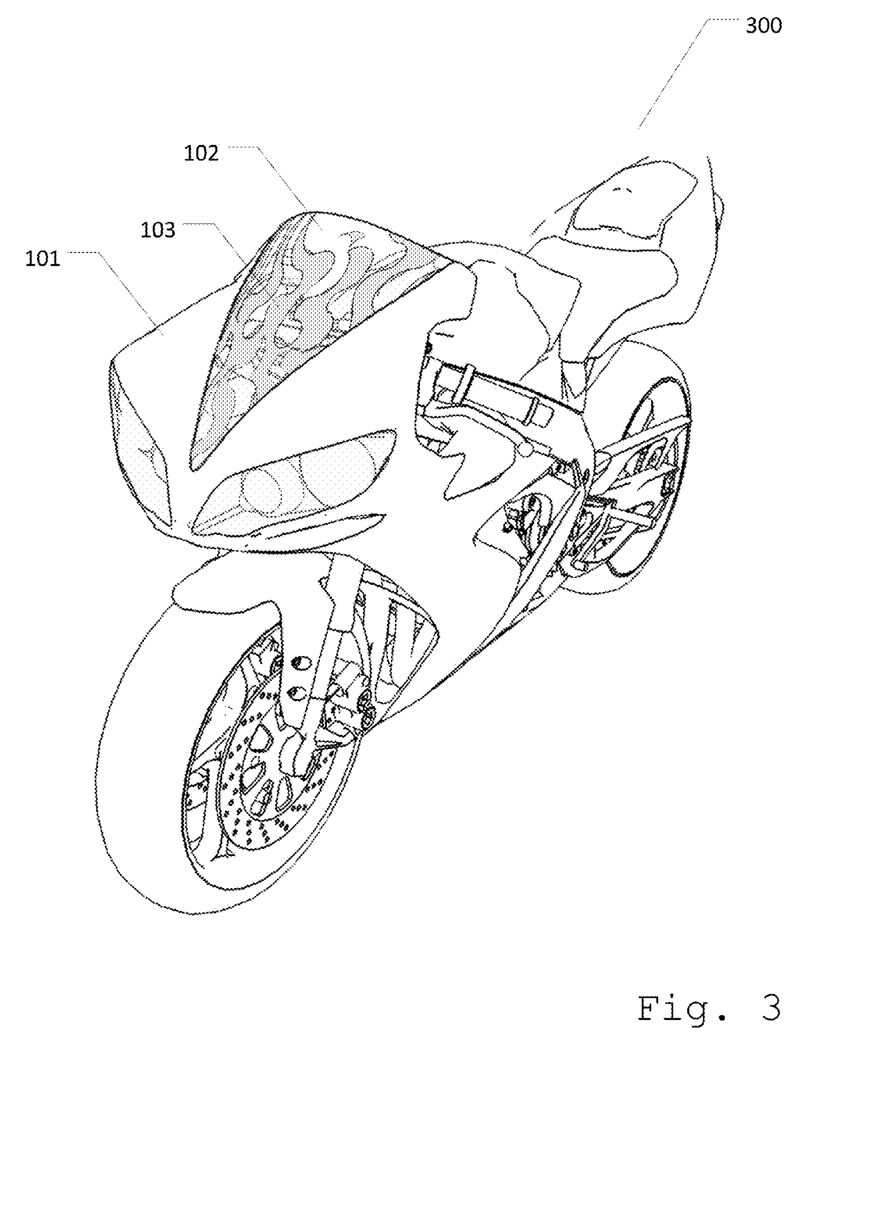
FIG. 3 illustrates a motorcycle with a hologram.

FIG. 3 illustrates a motorcycle 300 with hologram 103. For the purpose of this disclosure, motorcycle 300 can be a type of motor vehicle that can be used for transportation. Motorcycle 300 can be a two or three wheeled motorized vehicle such as ATVs, scooters, or dirt bikes. Motorcycle 300 can comprise body 101 and shield 102. Body 101 can be the main structure of motorcycle 300 wherein shield 102 can be attached. In this embodiment, shield 102 can be a windshield of motorcycle 300 placed at the front portion of motorcycle 300. Shield 102 can be used to personalize the look of motorcycle 300. As such, hologram 103 can be applied to shield 102 to enhance the appearance of motorcycle 300.

Figure 4:
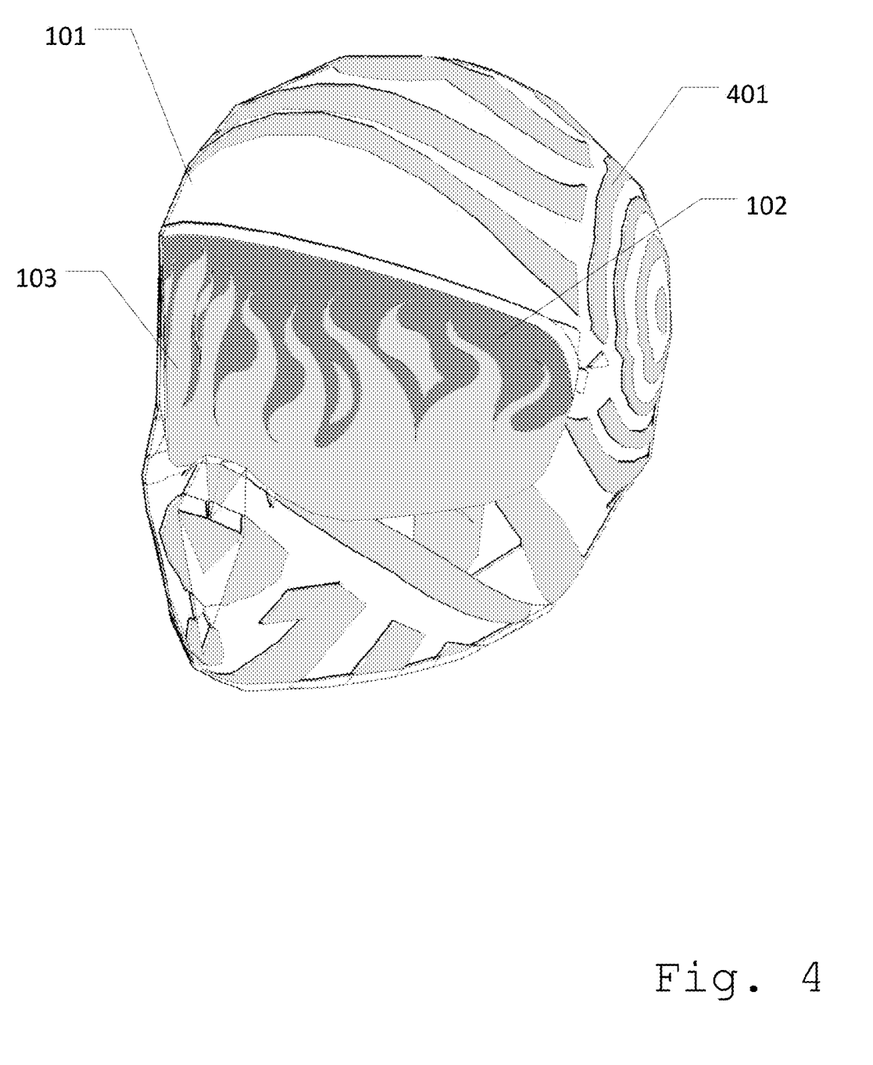
FIG. 4 illustrates the integration of a hologram with a design of a motorcycle helmet.

FIG. 4 illustrates the integration of hologram 103 with a design 401 of motorcycle helmet 100. Design 401 can be any two dimensional (2D) decoration that can be implemented through drawing, printing, painting, engraving, and/or embossing. As such, design 401 can complement the appearance of any structure or material. Design 401 can be used in body 101 of motorcycle helmet 100. In this embodiment, hologram 103 on shield 102 can be integrated with design 401. Hologram 103 can add to the interesting look of motorcycle helmet 100 especially when exposed or concealed from light. In a scenario wherein motorcycle helmet 100 is worn outdoor at day time, hologram 103 can appear and blend with design 401 of motorcycle helmet 100. Conversely, hologram 103 can fade out at night thus only design 401 can be visible during this time.

Figure 5:
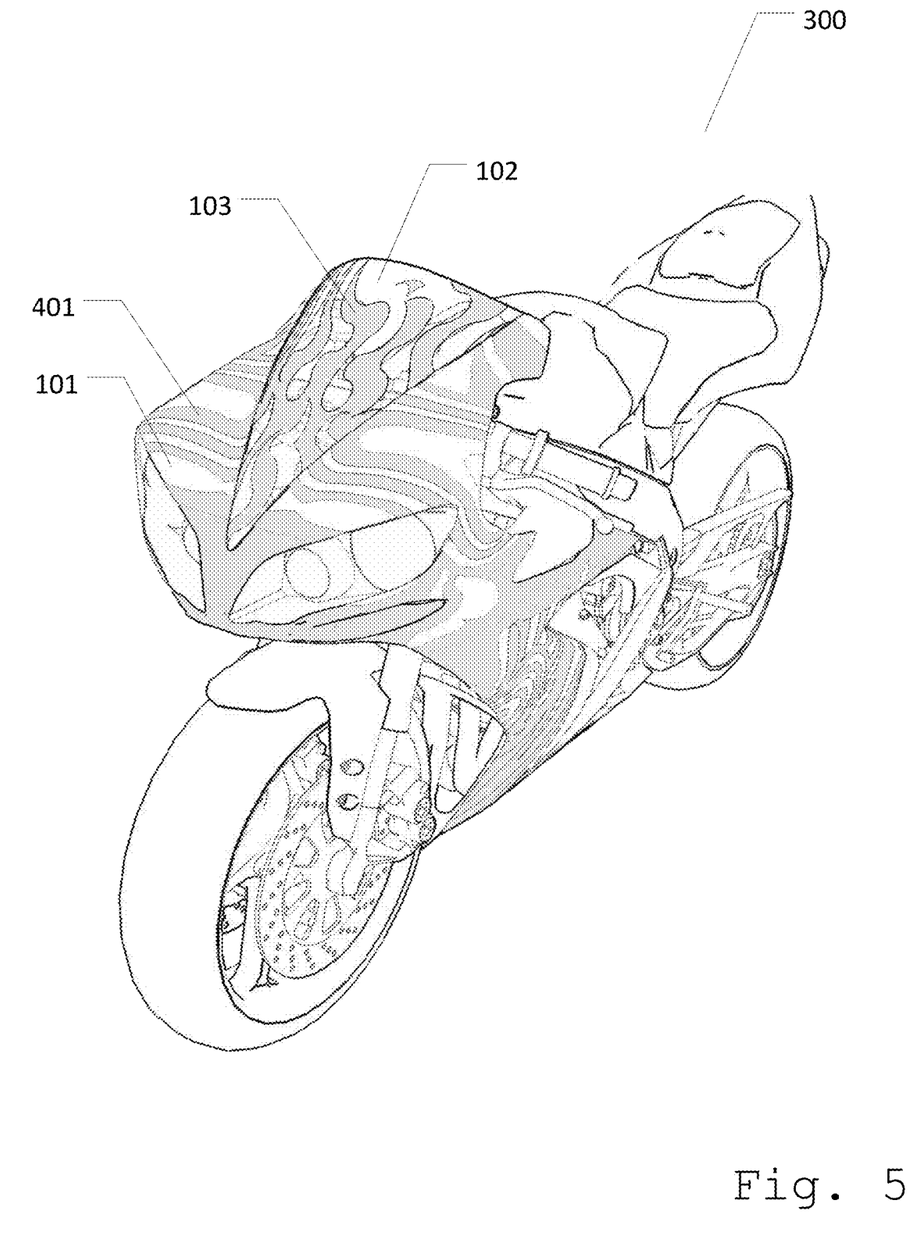
FIG. 5 illustrates a motorcycle that integrates a hologram with a motorcycle's design.

FIG. 5 illustrates motorcycle 300 that integrates hologram 103 with the motorcycle's design 401. In this embodiment, design 401 can be placed on body 101 of motorcycle 300. Hologram 103 employed on shield 102 can complement design 401 applied on body 101 of motorcycle 300. When motorcycle 300 is used at day time wherein motorcycle 300 is exposed to direct sunlight, hologram 103 can be visible therefore improving the overall appearance of motorcycle 300 during this time. Contrarily, at dusk or at night hologram 103 on shield 102 can disappear or can be barely visible to onlookers.

Figure 6:
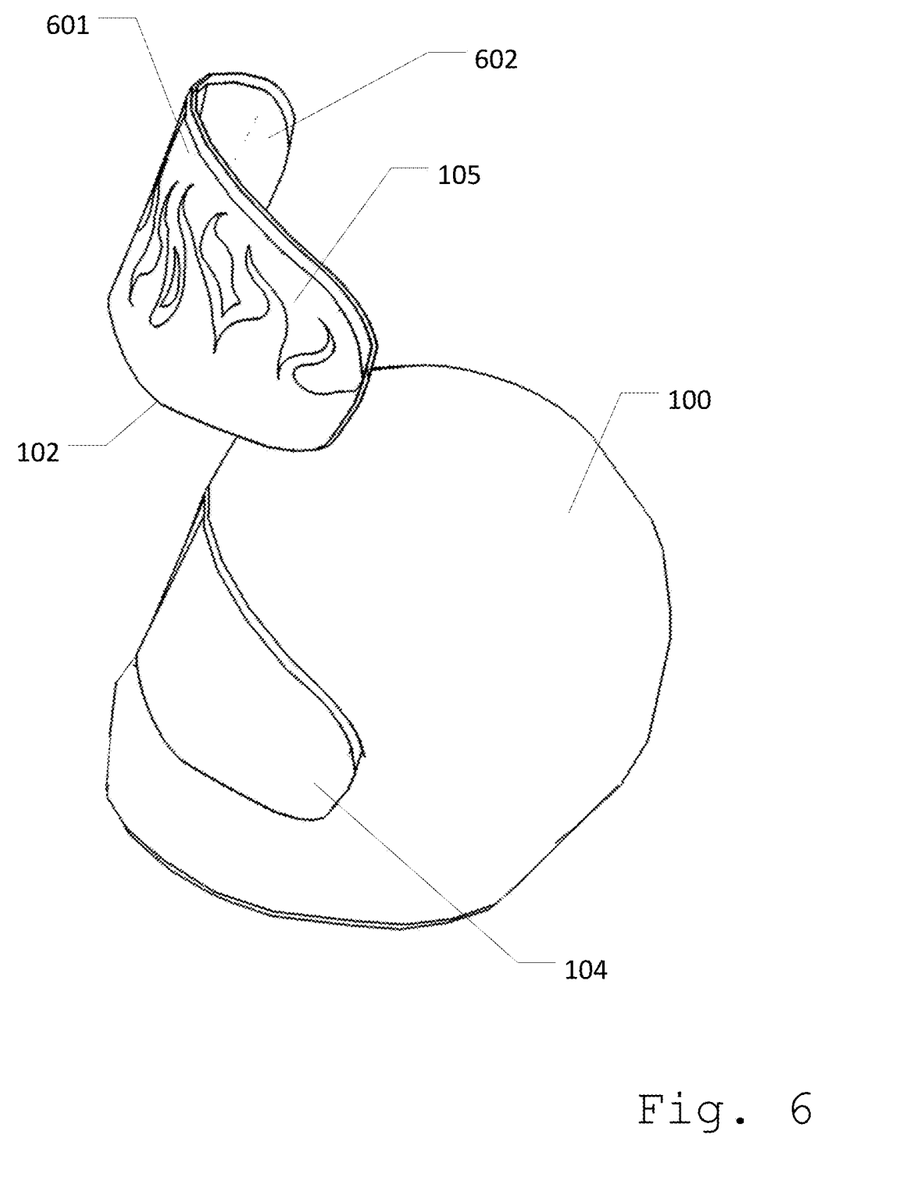
FIG. 6 illustrates an embodiment of a second layer, wherein a second layer can be removable from a motorcycle helmet.

FIG. 6 illustrates an embodiment of second layer 105, wherein second layer 105 can be removable from motorcycle helmet 100. Second layer 105 can comprise a top surface 601 and a bottom surface 602. Top surface 601 can be the portion of second layer 105 that comprises hologram 103. Bottom surface 602 can be the portion of second layer 105 that connects with the top surface of first layer 104. In one embodiment, second layer 105 can be attached to first layer 104 with a clear adhesive. In such embodiment, second layer 105 can self-adhere with first layer 104. Moreover, second layer 105 in this embodiment can utilize peel and stick method wherein second layer 105 can be removed and reapplied on top of first layer 104 numerous times. In another embodiment, second layer 105 can be printed on a statically connectable material and placed on top of first layer 104. In such embodiment, second layer can be positioned and connect to first layer without the use of adhesives. Such embodiment has the added benefit of being easier to remove and reattach. In such embodiment a different second layer 105 that comprises a different holographic design can be placed on first layer 104.

Figure 7:
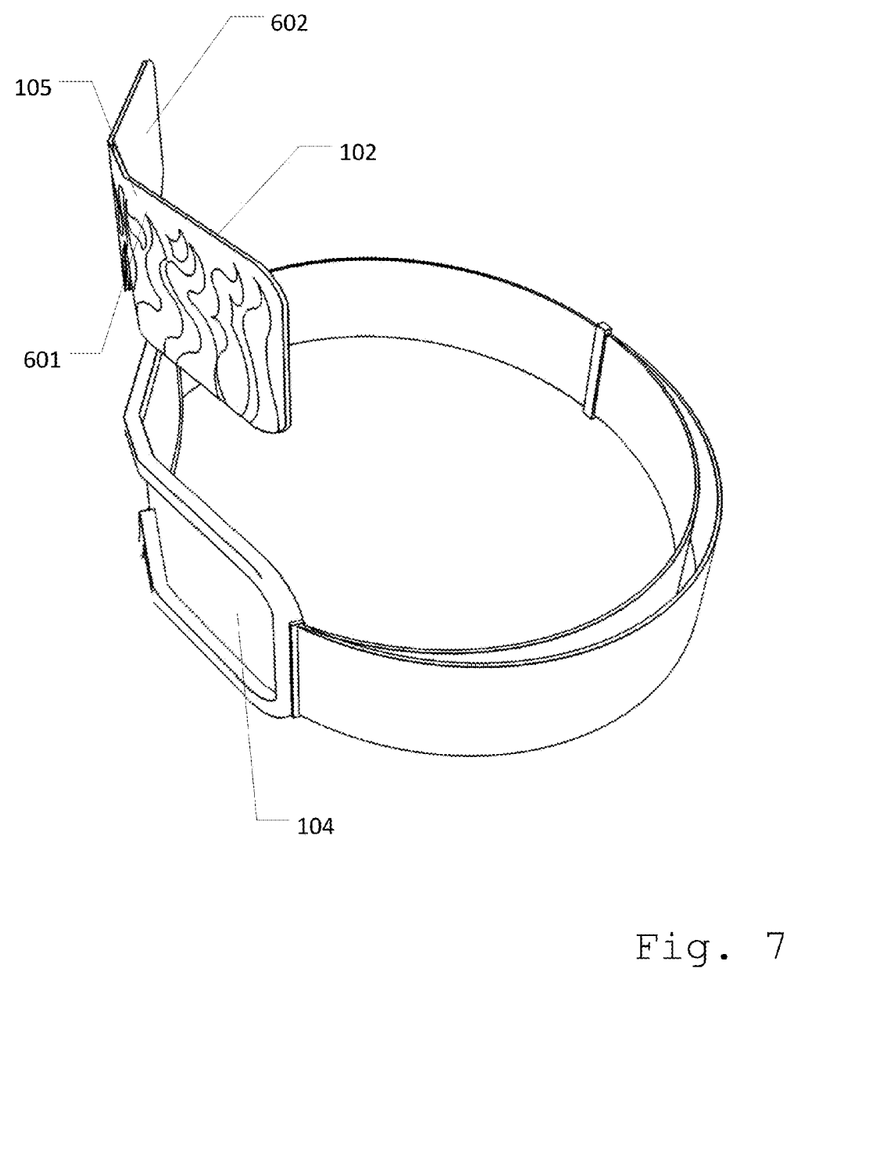
FIG. 7 illustrates an embodiment of a second layer, wherein a second layer can be removable from goggles.

FIG. 7 illustrates an embodiment of second layer 105, wherein second layer 105 can be removable from goggles 200. Second layer 105 of shield 102 on goggles 200 can be interchangeable. As such, a different hologram 103 design can be used on another second layer 105. In one embodiment, second layer 105 can be removed and reapplied at the top of first layer 104 through peel and stick method. In such embodiment, bottom portion 602 of second layer 105 can comprise of clear adhesive. As such second layer 105 can be removed and reapplied on top of first layer 104 numerous times. In another embodiment, second layer 105 can be printed on a statically connectable material and placed on top of first layer 104. Further in another embodiment, shield 102 can be interchangeable. In this embodiment, the whole shield 102 can be replaced instead of just the second layer 105. As such, second layer 105 can be permanently attached to first layer 104.

Figure 8A:
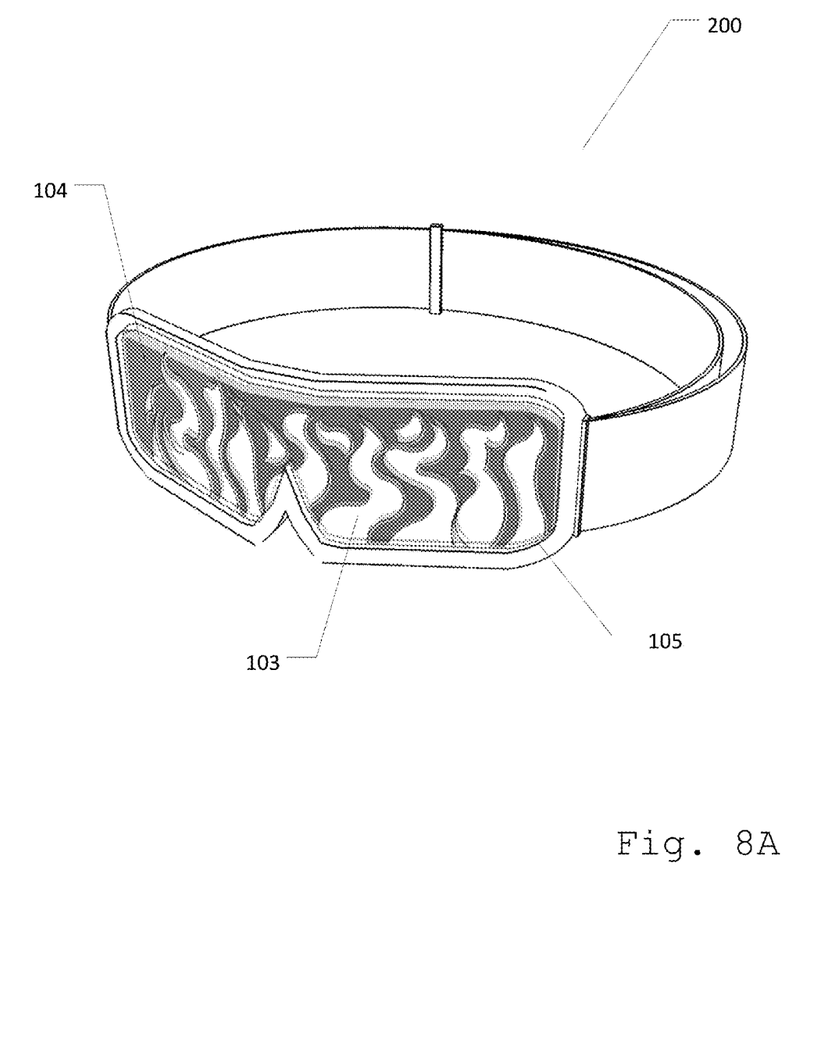
FIG. 8A illustrates a hologram on goggles when a first layer is more opaque.

FIG. 8A illustrates hologram 103 on goggles 200 when first layer 104 is more opaque. The projection of hologram 103 can adjust depending on the amount of exposure of goggles 200 from sunlight. When goggles 200 are exposed or placed in direct sunlight, first layer 104 becomes darker or more opaque. First layer 104 or photochromic materials rely on organic photochromic molecules, wherein at the exposure of sunlight, first layer 104 can absorb ultraviolet radiation causing first layer 104 to darken. Therefore, as first layer 104 becomes darker, hologram 103 on second layer 105 can appear more vibrant due to the reflective nature of the dark background.

Figure 8B:
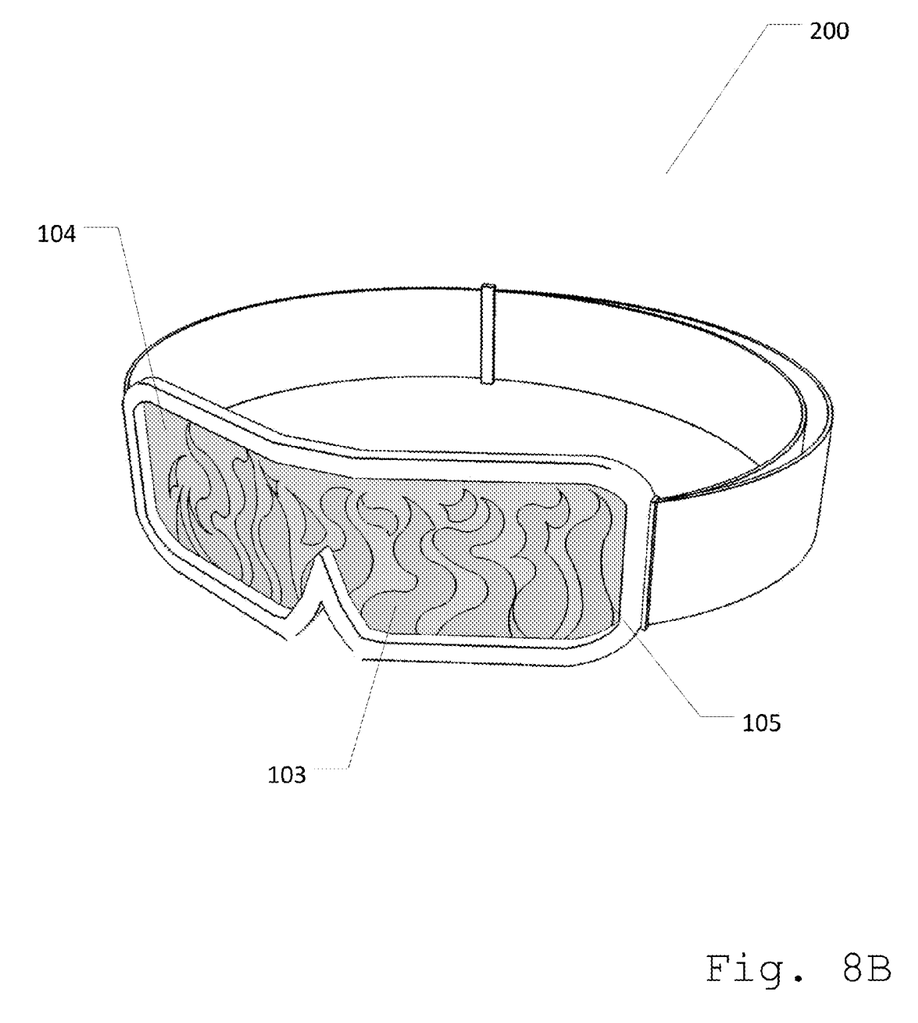
FIG. 8B illustrates a hologram on goggles when a first layer is clear.

FIG. 8B illustrates hologram 103 on goggles 200 when first layer 104 is clear. At a similar pattern, when goggles 200 are concealed from sunlight, the absence of ultraviolet radiation can cause first layer 104 to lighten and fade. Therefore, as ultraviolet on first layer 104 clears or fades out, hologram 103 on second layer 105 can lighten.

Figure 9A:
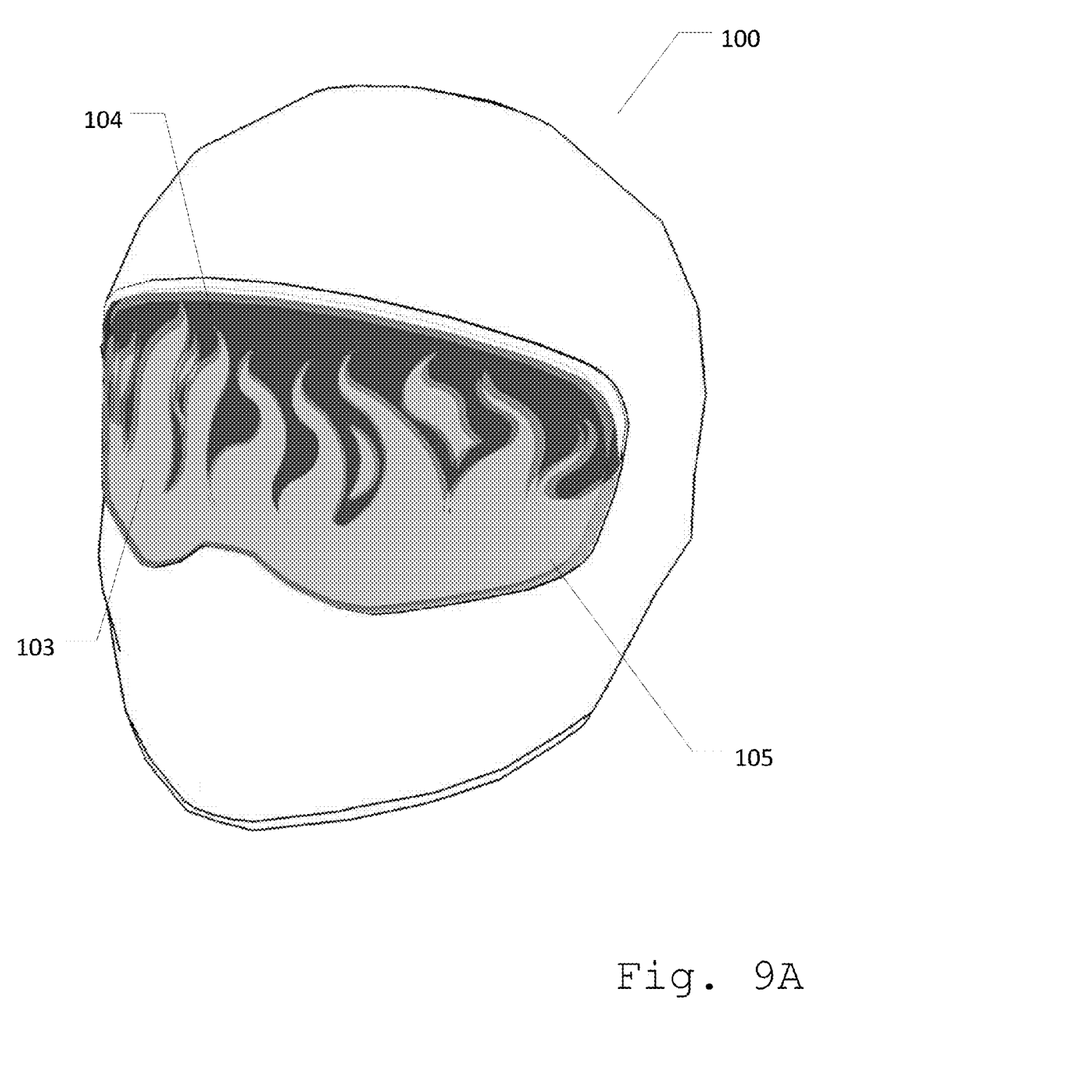
FIG. 9A illustrates a hologram on a motorcycle helmet when a first layer is more opaque.

FIG. 9A illustrates hologram 103 on motorcycle helmet 100 when first layer 104 is more opaque. In a scenario wherein motorcycle helmet 100 are exposed or placed in direct sunlight, first layer 104 of shield 102 becomes more opaque. First layer 104 becomes darker as ultraviolet light is absorbed. Therefore as first layer 104 becomes darker, hologram 103 on second layer 105 can appear more vibrant.

Figure 9B:
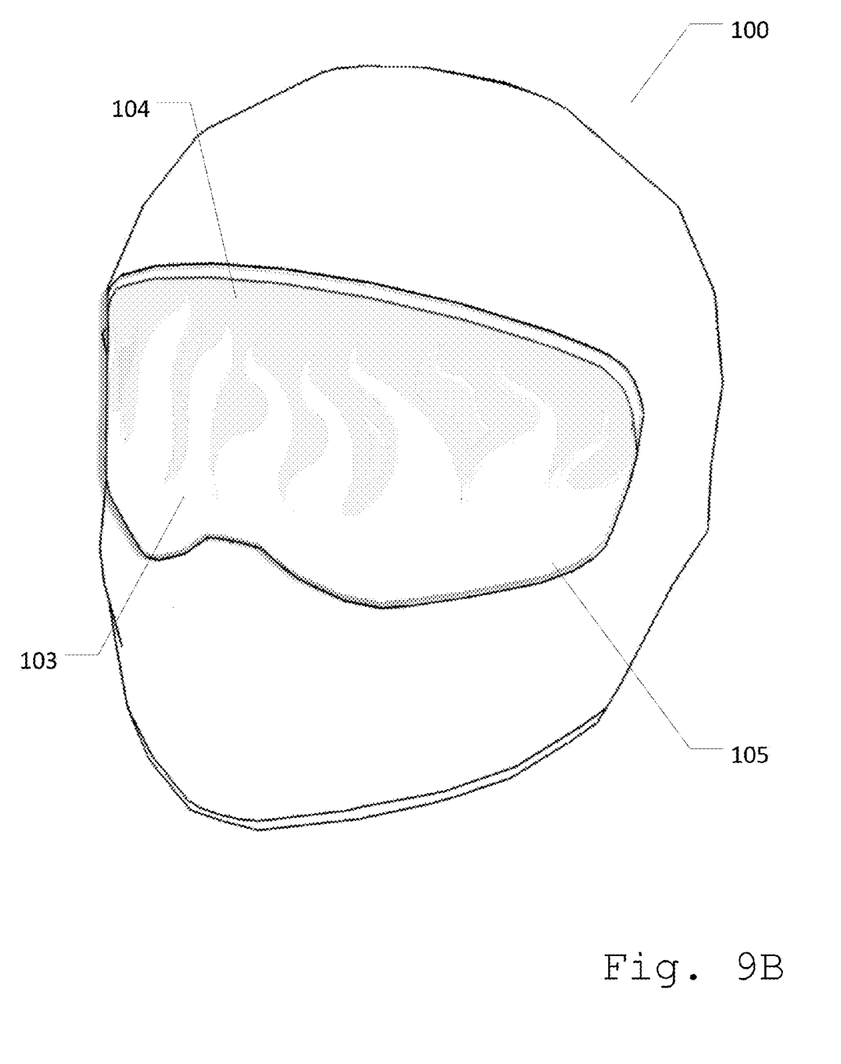
FIG. 9B illustrates a hologram on a motorcycle helmet when a first layer is clear.

FIG. 9B illustrates hologram 103 on motorcycle helmet 100 when first layer 104 is clear. Hologram 103 on second layer 105 can lighten when there is an absence of sunlight or ultraviolet rays. Therefore, hologram 103 can be barely visible during night time or when the weather is cloudy. This can be the result of the absence of ultraviolet radiation, which causes first layer 104 to lighten and fade.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A system for varying hologram visibility comprising a shield, said shield comprising
    a first layer comprising a photochromic material capable of transitioning between a darkened or more opaque state and a lightened or less opaque state; and
    a second layer comprising a hologram, said hologram less visible when said first layer is in said lightened or less opaque state; and
    a motorcycle helmet body, said shield connected to said motorcycle helmet body, said first layer facing the interior of said body, and said second portion facing the exterior of said body.

2. The system of claim 1 comprising an adhesive that attaches said first layer to said second layer.

3. The system of claim 2 wherein said adhesive comprises a statically connectable material.

4. The system of claim 1 wherein said shield is detachable and reattachable to said helmet body.

5. The system of claim 1 wherein said second layer is detachable and reattachable from said first layer.

6. A system for varying hologram visibility comprising a shield, said shield comprising
    a first layer comprising a photochromic material capable of transitioning between a darkened or more opaque state and a lightened or less opaque state; and
    a second layer comprising a hologram, said hologram less visible when said first layer is in said lightened or less opaque state; and
    a motorcycle body, said shield connected to said motorcycle body, said first layer facing a seat.

7. The system of claim 6 wherein said shield is detachable and reattachable to said motorcycle body.

8. The system of claim 7 wherein said second layer is detachable and reattachable from said first layer.

9. The system of claim 1 wherein said shield is a flexible material connectable to a transparent material.

10. A method for varying hologram visibility comprising attaching a second layer to a first layer, said first layer comprising a photochromic material capable of transitioning between a darkened or more opaque state and a lightened or less opaque state, and said second layer comprising a hologram, said hologram less visible when said first layer is in said lightened state, wherein said first layer is at least a portion of a motorcycle shield, said first layer facing the interior side of said motorcycle shield.

11. The method of claim 10, comprising the additional step of detaching said second layer from said first layer, and reattaching said first layer to said second layer.

12. The method of claim 11 wherein said second layer statically attaches to said second layer.

13. The method of claim 10 comprising the additional step of detaching said second layer from said first layer and reattaching a different second layer to said first layer.

* * * * *